United States Patent [19]

Field et al.

[11] 4,076,759

[45] Feb. 28, 1978

[54] PRODUCTION OF PHENOLS

[75] Inventors: Peter Graham Spencer Field, St-Foy-les-Lyons, France; Ronald Bennett, Chester, England

[73] Assignee: Burmah Oil Trading Limited, Wirral, Great Britain

[21] Appl. No.: 574,756

[22] Filed: May 5, 1975

[30] Foreign Application Priority Data

May 6, 1974 United Kingdom ............... 19806/74

[51] Int. Cl.² ...................... C07C 37/08; C07C 39/06; C07C 45/08
[52] U.S. Cl. ............................ 260/621 C; 260/624 R; 260/586 R
[58] Field of Search ........... 260/621 C, 621 R, 624 R, 260/624 C, 586 R

[56] References Cited

U.S. PATENT DOCUMENTS

| | | | |
|---|---|---|---|
| 2,661,375 | 12/1953 | Connor ................................. | 260/601 |
| 2,671,809 | 3/1954 | Filar ................... | 260/621 C |
| 2,683,751 | 7/1954 | Fortuin ........................... | 260/621 C |
| 2,889,368 | 6/1959 | Hiratsuka et al. .................... | 260/593 |
| 3,928,477 | 12/1975 | Field et al. ........................ | 260/621 C |

Primary Examiner—James O. Thomas, Jr.
Assistant Examiner—Werren B. Lone
Attorney, Agent, or Firm—Browdy and Neimark

[57] ABSTRACT

Phenols are prepared by decomposing secondary aromatic hydroperoxides in the presence of a compound comprising at least one metal atom or cation or at least one non-metallic cation and at least one moiety derivable from an anion of the formula

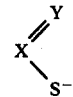

I wherein S is a sulphur atom; Y represents an atom of sulphur or oxygen, or a group of the formula =V—R' wherein V represents an atom of nitrogen or phosphorus and R' is a hydrogen atom or a substituted or unsubstituted hydrocarbyl group; and X is a group of the formula

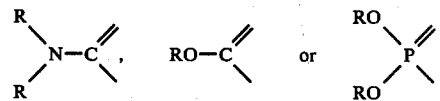

wherein each R represents a substituted or unsubstituted hydrocarbyl group and recovering the required phenol or substituted phenol from the decomposition product.

23 Claims, No Drawings

PRODUCTION OF PHENOLS

This invention relates to a process for the production of phenols by decomposing aromatic organic hydroperoxides.

Phenol is commonly produced on a large scale by decomposing cumene hydroperoxide in the presence of an acid catalyst, for example, sulphuric acid or perchloric acid. The mechanism of the reaction, when catalyzed by sulphuric acid is believed to be as follows:

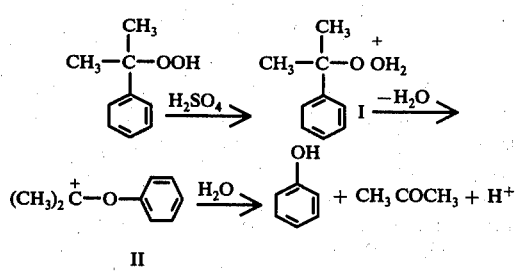

Thus the cumene hydroperoxide is protonated to form an intermediate I which loses water and rearranges to form the intermediate II which reacts with water to yield phenol and acetone.

The hydroperoxide is normally formed by autoxidation of cumene (isopropylbenzene) and the latter can be formed by alkylation of benzene with propylene. Other tertiary aralkyl hydroperoxides can be decomposed in the presence of acid catalysts to yield substituted phenols. Thus, for example, paracresol has been prepared by decomposing para-cymene hydroperoxide.

While the use of conventional acid catalysts to catalyze the decomposition of tertiary aralkyl hydroperoxides to phenols and ketones has led to reported yields of up to about 90 wt % phenol and 80 wt % ketone, based on the hydroperoxide it has not hitherto been considered commercially practicable to effect the decomposition of hydroperoxides other than tertiary aralkyl hydroperoxides, since firstly the yields of phenols produced have been commercially unattractive and secondly, undesirable quantities of high molecular weight by-products are produced when conventional acid catalysts are used.

A further disadvantage of the use of conventional acid catalysts is that it is generally necessary to construct the plant used to carry out the decomposition from corrosion-resistant materials and this can result in high capital costs. Furthermore, it is generally necessary to remove or neutralize the acid catalyst before the decomposition products are processed to recover phenol.

We have now discovered novel catalysts for this process the use of which enables the yields of phenols or substituted phenols from secondary aralkyl hydroperoxides to be raised to a level which makes this route to the phenols or substituted phenols commercially attractive. Use of the catalysts may additionally reduce the quantity of high molecular weight by-products formed during the decomposition reaction. Also, since the catalysts are not strongly acidic in nature, the vessels used for carrying out the decomposition need not be constructed of such corrosion-resistant materials as are required when acid catalysts are used and there is also no need to remove the catalyst before the phenols are recovered, although this may be effected if desired.

According to the present invention, there is provided a process for producing a phenol or a substituted phenol by decomposing a secondary aromatic organic hydroperoxide, which process comprises effecting the decomposition in the presence of a catalyst comprising a compound comprising at least one metal atom or cation or at least one non-metallic cation and at least one moiety derivable from an anion of the formula

wherein S is a sulphur atom; Y represents an atom of sulphur or oxygen, or a group of the formula $$=V-R'$$

wherein V represents an atom of nitrogen or phosphorus and R' is a hydrogen atom or a substituted or unsubstituted hydrocarbyl group; and X is a group of the formula

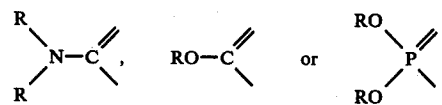

wherein each R represents a substituted or unsubstituted hydrocarbyl group, preferably containing from 1 to 12 carbon atoms, and recovering the required phenol or substituted phenol from the decomposition product. Preferably, on account of the facility with which such compounds are prepared, the catalyst comprises a compound as defined above where Y is an atom of sulphur.

Examples of unsubstituted hydrocarbyl groups R and R' are alkyl groups (both straight chained and branched), aryl groups (including alkaryl groups) and aralkyl groups, for example benzyl groups. Preferred alkyl groups are those containing from 1 to 8, such as, for example, methyl, ethyl, propyl, iso-propyl, n-butyl, iso-butyl, t-butyl, aryl, heptyl and octyl, and preferably those containing from 1 to 4 carbon atoms.

Examples of non-metallic cations include ammonium ions ($NR_4^+$) wherein each R is hydrogen or a group as defined above.

Examples of substituted hydrocarbyl groups are hydrocarbyl groups, for example those referred to above, substituted by one or more halogen atoms, alkoxy groups, which preferably contain from 1 to 6 carbon atoms, or nitro groups.

Preferably, the catalyst comprises a compound of a transition metal, in particular a compound of transition metals appearing in Group VIII, Group Ib or Group IIb of the Periodic Table, although compounds of non-transitional metals, for example of tin or antimony may also be used.

Thus, for example, the catalysts may comprise a compound comprising at least one moiety derivable from an anion of formula (I) defined above and at least one metal atom selected from iron, cobalt, nickel, palladium, copper, silver, zinc, cadmium, mercury, tin and antimony atoms.

The structure of the metal compound used as catalyst in the process of the invention depends, of course, on the identity of the metal and of the groups X and Y.

Thus, for example, the compounds may be complexes, as represented by the formula

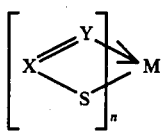  II wherein M is the metal and n is the oxidation state of the metal, or they may be a compound which is salt-like in nature as represented by the formula

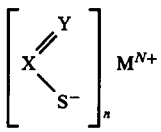  III wherein n is as defined above.

With certain metals, the compounds are believed to be polymeric, for example, as represented by the formula

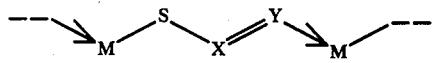  IV

Thus, for example, the compounds may consist of linear chains of metal atoms and ligands, or chains of metal atoms and ligands forming a three-dimensional polymer.

Thus it can be seen that the moieties derivable from the anion of formula (I) may be the ligand portion of a complex or the anion portion of a salt.

Representative examples of classes of catalyst which may be used in the process of the invention are metal N-disubstituted mono- and dithiocarbamates which may be represented by the formula

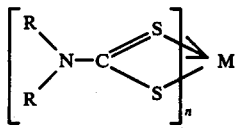  V and

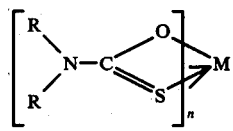  VI wherein M is the metal, n is the oxidation state of the metal and R is as defined above; metal xanthates, which may be represented by the formula

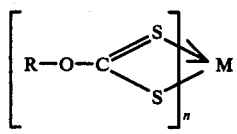  VII wherein M is the metal, n is oxidation state of the metal and R is as defined above; and metal di-substituted di- and monothiophosphates; which may be represented by the formula

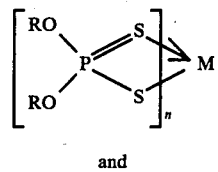  VIII and

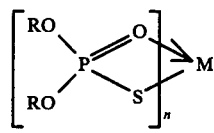  IX wherein M is the metal, n is the oxidation of the metal and R is defined above.

Particularly preferred catalysts are compounds of general formulae V, VI, VII, VIII and IX wherein each group R represents an alkyl group, particularly the alkyl groups specifically referred to above.

It has been observed surprisingly that by using the process of the invention, increased yields of phenols may be obtained by decomposing secondary aromatic organic hydroperoxides than when conventional acid catalysts are used. Thus, for example, yields in excess of 80 wt % of phenol have been obtained by decomposing ethylbenzene hydroperoxide in accordance with the process of the invention. Furthermore, significantly lower quantites of high molecular weight by-products are formed than when conventional acid catalysts are used.

The secondary aromatic organic hydroperoxide starting material employed in the process of the present invention may be an aryl mono-alkyl hydroperoxide, which perferably contains from 2 to 24, more preferably 2 to 16 and especially 2 to 12 carbon atoms in the alkyl moiety. An example of such a hydroperoxide is ethyl benzene hydroperoxide. Alternatively, a substituted -aryl alkyl hydroperoxide may be used, i.e. a hydroperoxide in which the aryl group bears one or more substituents e.g. selected from halogen atoms and alkyl, alkoxy and nitro groups. Decomposition of such hydroperoxides produces a correspondingly substituted phenol. In yet another alternative a dialkylaryl dihydroperoxide may be used, i.e. a compound having an aryl nucleus substituted by two secondary alkylhydroperoxide groups, in which case a dihydric phenol will result from the decomposition. Such hydroperoxides may likewise bear one or more substituents thus enabling correspondingly substituted dihydric phenols to be obtained.

The decomposition of the hydroperoxide in the presence of the catalyst proceeds very readily and may be carried out under a wide variety of reaction conditions. Preferably the reaction temperature is not permitted to reach too high a level since this could lead to the thermally initiated decomposition of the hydroperoxide, producing undesirable by-products, and in an extreme case might lead to decomposition becoming too rapid and uncontrollable, and potentially explosive. A reaction temperature of from ambient to 180° C is preferred, more preferably ambient to 150° C and especially 100° C to 140° C. The decomposition of the hydroperoxide may be sufficiently exothermic to make it desirable to control the reaction temperature in order to maintain it at the desired level. Conventional techniques can be used for this purpose, such as external cooling and/or regulating the rate at which the hydroperoxide is brought into contact with the catalyst.

Preferably the aldehyde co-product of the decomposition is continuously removed during the decomposition reaction in order to reduce the possibility of unwanted side reactions between the aldehyde and other components of the decomposition product. Thus, for example, the aldehyde may be distilled off and collected in a condenser. Removal of the aldehyde may be assisted by conducting the decomposition under reduced pressure, but generally the pressure at which the decomposition is carried out is not narrowly critical and conveniently atmospheric pressure may be used, particularly in the case where the co-product aldehyde is sufficiently volatile at the reaction temperature to be distilled off at atmospheric pressure.

The time required for completion of the reaction will depend, inter alia, on the reaction temperature but even at very low reaction temperatures is normally not more than 3 or 4 hours. At preferred reaction temperatures the decomposition will in most cases be completed within, e.g. 5 to 50 minutes at 150° C or within 1½ to 2 hours, usually not more than 1 hour, at 80° C to 120° C.

In order to moderate the decomposition, the process of the present invention is generally carried out in the presence of an inert solvent, i.e. a solvent which does not react with the hydroperoxide or its decomposition products. Thus in the case of a hydroperoxide which is solid at the reaction temperature it is preferred to dissolve the hydroperoxide in an inert solvent. The inert solvent can also be used if desired even when the hydroperoxide is liquid at the reaction temperature used. If used, the inert solvent is preferably present in an amount such as to provide a solution containing from 1% to 50%, more preferably 5% to 25%, by weight of the hydroperoxide. Examples of inert solvents include benzene, toluene, xylene, ethylbenzene, chlorobenzene and nitrobenzene.

Very small quantities of the catalyst may be successfully employed in the process of the present invention. Larger quantities can also be used. However, this is unnecessary and wasteful and in some cases larger quantities of catalyst maybe detrimental. In a preferred embodiment of the invention the ratio of catalyst to hydroperoxide is from 1:10,000 to 1:1000, preferably 1:5,000 to 1:1,000.

The hydroperoxides used in the process of the present invention may be prepared by the usual methods, such as autoxidation of an alkyl aryl compound. The alkyl aryl starting materials for the autoxidation may also be prepared by the usual methods such as alkylation of aryl compounds with an olefin.

The phenol and the aldehyde produced in accordance with the process of the invention may be recovered by conventional methods, for example by fractional distillation and in general the purification techniques used in the conventional acid-catalyzed process may be employed, although of course the process steps concerned with the removal of the catalyst may be omitted.

The invention will now be illustrated by the following Examples:

EXAMPLE 1

0.0025 parts by weight of bis(diethyldithiocarbamato) cobalt (II) (molecular weight 355.5) was weighed into a glass pressure vessel and dissolved in 25 parts by weight of ethylbenzene.

3 parts by weight of ethylbenzene hydroperoxide (mole ratio of ethylbenzene hydroperoxide to catalyst = 3000:1) was added and the pressure vessel sealed.

The reactor was heated on an oil bath maintained at 120° C for 30 minutes whilst agitating the contents using a magnetic follower.

The contents were cooled, and analyzed for residual hydroperoxide and phenol.

The following analysis was obtained:

| | |
|---|---|
| Residual Hydroperoxide | 0.03 parts by weight |
| Phenol produced | 1.62 parts by weight |
| Percentage conversion | 99.0% |
| Selectivity to Phenol | 82.7% |

EXAMPLES 2 to 14

The procedure of Example 1 was repeated using various catalysts and the results are shown in the following Table.

TABLE

| Example | Catalyst | Molecular weight of Catalyst | Parts by weight of Catalyst | Ethylbenzene Hydroperoxide to Catalyst Ratio | Residual Hydroperoxide (parts by weight) | Mass of Phenol produced (parts by weight) | Percentage Conversion | Percentage Selectivity to Phenol |
|---|---|---|---|---|---|---|---|---|
| 2 | Tris(diethyldithio carbamato) Iron (III) | 500.6 | 0.0034 | 3115:1 | 0.14 | 1.19 | 95.2 | 63.0 |
| 3 | Bis(diethyldithiocarbamato) Nickel (II) | 355.3 | 0.0025 | 3000:1 | 0.04 | 1.50 | 98.6 | 76.9 |
| 4 | Bis(diethyldithiophosphato) Nickel (II) | 429.1 | 0.0030 | 2984:1 | 0.01 | 1.67 | 99.9 | 84.0 |
| 5 | Bis(ethylxanthato) Nickel (II) | 301.1 | 0.0021 | 2976:1 | 0.15 | 1.24 | 94.8 | 66.5 |
| 6 | Bis(diethyldithiocarbamato) Copper (II) | 360.1 | 0.0025 | 2963:1 | 0.02 | 1.52 | 99.3 | 77.2 |
| 7 | Bis(dibenzyldithiocarbamato) Zinc (II) | 554 | 0.0044 | 2655:1 | 0.03 | 1.59 | 99.0 | 81.0 |
| 8 | Bis(diethyldithiocarbamato) Palladium (II) | 402.9 | 0.0028 | 2966:1 | 0.07 | 1.43 | 97.6 | 74.1 |
| 9 | Mono (diethyldithiocarbamato) Silver (I) | 256.1 | 0.0018 | 3000:1 | 1.46 | 0.53 | 49.8 | 53.5 |
| 10 | Bis(dibutyldithiocarbamato) Cadmium (II) | 521.9 | 0.0037 | 3026:1 | 0.03 | 1.61 | 99.0 | 81.6 |
| 11 | Bis(diethyldithiocarbamato) Mercury (II) | 497.1 | 0.0035 | 3005:1 | 0.02 | 1.67 | 99.3 | 84.8 |

TABLE-continued

| Example | Catalyst | Molecular weight of Catalyst | Parts by weight of Catalyst | Ethylbenzene Hydroperoxide to Catalyst Ratio | Residual Hydroperoxide(parts by weight) | Mass of Phenol produced(parts by weight) | Percentage Conversion | Percentage Selectivity to Phenol |
|---|---|---|---|---|---|---|---|---|
| 12 | Bis(diethyldithiocarbamato) Tin (II) | 415.2 | 0.0026 | 3367:1 | 0.03 | 1.66 | 99.0 | 84.6 |
| 13 | Tetrakis-(diethyldithiocarbamato) Tin (IV) | 711.7 | 0.0051 | 2939:1 | 0.03 | 1.49 | 99.0 | 75.8 |
| 14 | Tris(diethyldithiocarbamato) Antimony (III) | 566.6 | 0.0039 | 3045:1 | 0.01 | 1.58 | 99.7 | 79.5 |

We claim:

1. In the process comprising decomposing a secondary aralkyl hydroperoxide, in which the aryl nucleus is substituted by at least one secondary alkylhydroperoxide group containing from 2 to 24 carbon atoms and said aryl nucleus may be further substituted by one or more other substituents selected from halogen atoms and alkyl, alkoxy and nitro groups, to produce a correspondingly substituted or unsubstituted mono- or polyhydric phenol, the improvement comprising:

effecting the decomposition at a temperature of from ambient temperature to 180° C in the presence of a catalysts comprising a complex having the formula

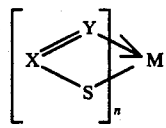

wherein Y represents an atom of sulphur or oxygen, M is tin, antimony or a transition metal appearing in Group VIII, Ib or IIb of the Periodic Table. N is the oxidation state of M, and X is selected such that said formula is

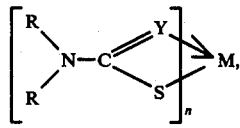

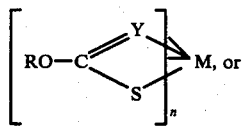

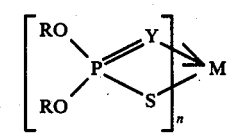

wherein each R represents an unsubstituted hydrocarbyl group containing 1 to 12 carbon atoms; and recovering said correspondingly substituted or unsubstituted mono- or polyhydric phenol from the decomposition product.

2. A process according to claim 1 in which the catalyst comprises a metal N-disubstituted mono- or dithiocarbamate.

3. A process according to claim 1 in which the catalyst comprises a metal xanthate.

4. A process according to claim 1 in which the catalyst comprises a metal di-substituted di- or monothiophosphate.

5. A process according to claim 1 in which the M is a transistion metal.

6. A process according to claim 1 in which the aromatic hydroperoxide is an aryl mono-alkyl hydroperoxide containing from 2 to 24 carbon atoms in the alkyl moiety.

7. A process according to claim 6 in which the monoalkyl hydroperoxide contains from 2 to 12 carbon atoms in the alkyl moiety.

8. A process according to claim 7 in which the aromatic hydroperoxide is ethylbenzene hydroperoxide.

9. A process according to claim 1 in which the decomposition is carried out in the presence of an inert solvent.

10. A process according to claim 1 in which the ratio of catalyst to hydroperoxide is from 1:10,000 to 1:1,000.

11. A process according to claim 10 in which the ratio of catalyst to hydroperoxide is from 1:5,000 to 1:1,000.

12. A process according to Claim 1 in which M is a metal selected from the group consisting of iron, cobalt, nickel, palladium, copper, silver, zinc, cadmium, mercury, tin and antimony.

13. A process in accordance with claim 1 wherein said secondary aralkyl hydroperoxide is a secondary alkylbenzene hydroperoxide in which the benzene nucleus is substituted by at least one secondary alkylhydroperoxide group containing from 2 to 24 carbon atoms as well as zero or more other substituents selected from halogen atoms and alkyl, alkoxy and nitro groups.

14. A process in accordance with claim 1 wherein said secondary aralkyl hydroperoxide is a secondary aralkyl hydroperoxide in which the aryl nucleus is substituted by only one or two secondary alkylhydroperoxide groups, each containing from 2 to 24 carbon atoms, as well as zero or more other substituents selected from halogen atoms and alkyl, alkoxy and nitro groups, and wherein a correspondingly substituted or unsubstituted mono- or dihydric phenol is produced.

15. A process is accordance with claim 13 wherein said secondary alkylbenzene hydroperoxide is a secondary alkylbenzene hydroperoxide in which the benzene nucleus is substituted by one or two secondary alkylhydroperoxide groups, each containing from 2 to 24 carbon atoms as well as zero or more other substitutents selected from halogen atoms and alkyl, alkoxy and nitro groups, and wherein a correspondingly substituted or unsubstituted mono- or dihydric phenol is produced.

16. A process in accordance with claim 1 wherein said secondary aralkyl hydroperoxide is a secondary alkylbenzene hydroperoxide in which the benzene nucleus is substituted by at least one secondary alkylhydroperoxide group containing 2 to 24 carbon atoms, and is otherwise unsubstituted.

17. A process in accordance with claim 16 wherein said secondary alkylbenzene hydroperoxide is one in which the benzene nucleus is substituted by only one or two of said secondary alkylhydroperoxide groups.

18. A process in accordance with claim 17 wherein said secondary alkylbenzene hydroperoxide is one in which the benzene nucleus is substituted by only one of said secondary alkylhydroperoxide groups and wherein unsubstituted monohydric phenol is produced.

19. In the process comprising decomposing a secondary aralkyl hydroperoxide, in which the aryl nucleus is substituted by at least one secondary alkylhydroperoxide group containing from 2 to 24 carbon atoms and said aryl nucleus may be further substituted by one or more other substituents selected from halogen atoms and alkyl, alkoxy and nitro groups, to produce a correspondingly substituted or unsubstituted mono- or polyhydric phenol, the improvement comprising:
effecting the decomposition at a temperature of from ambient temperature to 180° C in the presence of a catalyst comprising a compound when in salt-like form having the formula

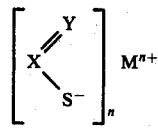

wherein Y represents an atom of sulphur or oxygen, M is a metal cation or a non-metallic cation, selected from the group consisting of transition metals appearing in Group VIII, Group Ib or Group IIb of the Periodic Table, tin, and antimony, or $NR'_4{}^+$ wherein each R' is hydrogen or an unsubstituted hydrocarbyl group containing 1 to 12 carbon atoms n is the oxidation state of M, and X is selected such that said formula is

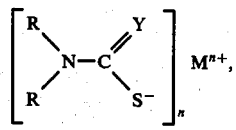

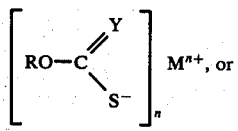

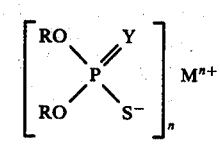

wherein each R represents an unsubstituted hydrocarbyl group containing 1 to 12 carbon atoms; and
recovering said correspondingly substituted or unsubstituted mono- or polyhydric phenol from the decomposition product.

20. A process according to claim 19 in which M is tin, antimony or a transition metal appearing in Group VIII, Group Ib or Group IIb of the Periodic Table.

21. A process according to claim 19 in which M is a metal selected from the group consisting of iron, cobalt, nickel, palladium, copper, silver, zinc, cadmium, mercury, tin and antimony.

22. In the process comprising decomposing a secondary aralkyl hydroperoxide, in which the aryl nucleus is substituted by at least one secondary alkylhydroperoxide group containing from 2 to 24 carbon atoms and said aryl nucleus may be further substituted by one or more other substituents selected from halogen atoms and alkyl, alkoxy and nitro groups, to produce a correspondingly substituted or unsubstitited mono- or polyhydric phenol, the improvement comprising:
effecting the decomposition at a temperature of from ambient tempcrature to 180° C in the presence of a catalyst comprising a polymeric compound as represented by the formula

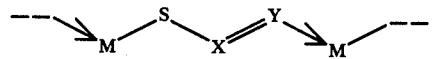

wherein Y represents an atom of sulphur or oxygen, M is tin, antimony or a transition metal appearing in Group VIII, Group Ib or IIb of the Periodic Table, and X is selected such that said formula is

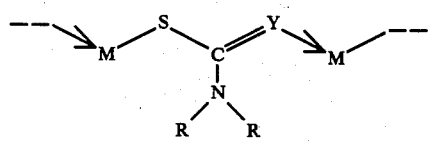

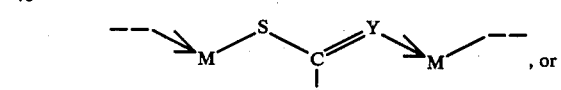, or

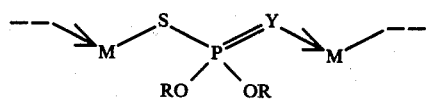

wherein each R represents an unsubstituted hydrocarbyl group containing 1 to 12 carbon atoms; and
recovering said correspondingly substituted or unsubstituted mono- or polyhydric phenol from the decomposition product.

23. A process according to claim 22 in which M is a metal selected from the group consisting of iron, cobalt, nickel, palladium, copper, silver, zinc, cadmium, mercury, tin and antimony.

* * * * *